(12) United States Patent
Karmalawy et al.

(10) Patent No.: US 6,603,991 B1
(45) Date of Patent: Aug. 5, 2003

(54) METHOD AND APPARATUS FOR DUAL MODE MEDICAL IMAGING SYSTEM

(75) Inventors: Moataz Karmalawy, San Ramon, CA (US); Mel Deane, Pleasanton, CA (US); Mark DeSilets, Cupertino, CA (US); Steve Nero, San Jose, CA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/449,171

(22) Filed: Nov. 24, 1999

(51) Int. Cl.$^7$ .................................................. A61B 5/05
(52) U.S. Cl. ........................ 600/411; 600/425; 600/427; 378/63
(58) Field of Search ................................ 600/407, 410, 600/411, 425, 427, 437; 324/303; 378/21, 4, 62, 63; 5/601; 128/906; 250/363.01–363.05

(56) References Cited

U.S. PATENT DOCUMENTS

| 5,155,365 | A | | 10/1992 | Cann et al. |
| 5,178,146 | A | * | 1/1993 | Giese ........................ 128/653.2 |
| 5,376,795 | A | | 12/1994 | Hasegawa et al. |
| 5,391,877 | A | * | 2/1995 | Marks .................... 250/363.03 |
| 5,537,452 | A | * | 7/1996 | Shepherd et al. ............ 378/148 |
| 5,851,182 | A | * | 12/1998 | Sahadevan .................... 378/63 |
| 5,897,495 | A | * | 4/1999 | Aida et al. ................... 600/411 |
| 6,094,590 | A | * | 7/2000 | Kan et al. .................... 600/411 |
| 6,205,347 | B1 | * | 3/2001 | Morgan et al. .............. 600/407 |

* cited by examiner

Primary Examiner—Marvin M. Lateef
Assistant Examiner—Jeoyuh Lin
(74) Attorney, Agent, or Firm—Eugene E. Clair (57) ABSTRACT

In one embodiment, the present invention includes a system including a CT system, an NM system, a NM bed operatively coupled to the NM system, and a CT bed operatively coupled to the CT system, with the CT bed coupled to the NM bed when the CT system is used for dual mode imaging.

9 Claims, 7 Drawing Sheets

METHOD AND APPARATUS FOR DUAL MODE MEDICAL IMAGING SYSTEM

BACKGROUND OF THE INVENTION

1. Field of the Invention

The invention relates to techniques and apparatus for performing multi-modal medical (diagnostic) imaging scans of a patient, including but not limited to Nuclear Medicine systems, CT (Computerized Tomography) systems, general X-Ray systems, Magnetic Resonance imaging (MRI) systems, ultrasound systems, sonograph systems, and the combination thereof. Each of these systems may be said to have a single mode or modality.

2. Description of the Related Art

CT (Computerized Tomography) systems are well known x-ray based medical imaging systems, and well used by the medical establishment to analyze injuries and diseases. Likewise, Nuclear Medicine (NM) gamma-ray based medical imaging systems are well known tomographic imaging systems, and used by the medical establishment to analyze injuries and diseases. Furthermore, Magnetic Resonance Imaging (MRI) systems are well known tomographic imaging systems, and well used by the medical establishment to analyze injuries and diseases. CT systems typically function by irradiating a patient with X-rays and recording the images generated thereby. Nuclear medicine systems typically function by recording the images from radiation such as gamma rays which are emitted by the patient. The patient emits this radiation as a result of irradiated material introduced into the patient's body prior to the nuclear medicine scan. In all of these systems, the act of acquiring data may be referred to as a scan.

Unfortunately, any one of these systems typically occupies nearly a whole room, and these systems are often controlled by different departments in a medical group such as a hospital (such as Radiology as opposed to Nuclear Medicine departments). Moreover, none of these systems are typically designed with any consideration for integration with other systems, so CT, NM, and MRI systems almost always are separated by significant distance if they are in the same building, and are often on separate floors.

However, integrating the data from a NM system with that from a CT or MRI system, or integrating the information from any two of these systems may lead to useful additional information, thus enhancing a medical staff member's ability to diagnose a patient's injuries or diseases, and determine a course of treatment. At this time, integration of such data is commonly handled by software programs, which must attempt to account for differences in position of the patient during data-gathering activities of each system. Since the patient must often move voluntarily from one system to another, or be helped in such a move, the patient is almost inevitably in a different position for a measurement or data gathering session in a second system from the position of the patient in the measurement session in a first system. Even if the patient is placed in the same position for two separate scans, the acts of moving into and out of that position typically cause the patient's organs to shift locations relative to each other. This change in position or change in internal position of organs introduces errors and complicates the process of comparing the data gathered from the two systems. The combination of physiological and functional image data for accurate diagnosis requires that the functional image be closely aligned with the physiological. This means that the relative distances between internal organs must be preserved. Any movement of the patient between scans makes such alignment impractical.

SUMMARY OF THE INVENTION

In one embodiment, the present invention includes a system including a CT system, an NM system, a NM bed operatively coupled to the NM system, and a CT bed operatively coupled to the CT system, with the CT bed coupled to the NM bed when the CT system is used for dual mode imaging.

BRIEF DESCRIPTION OF THE DRAWINGS

The present invention is illustrated by way of example and not limitation in the accompanying figures.

DETAILED DESCRIPTION

A method and apparatus for a dual mode medical imaging system is described. In the following description, for purposes of explanation, numerous specific details are set forth in order to provide a thorough understanding of the invention. It will be apparent, however, to one skilled in the art that the invention can be practiced without these specific details. In other instances, structures and devices are shown in block diagram form in order to avoid obscuring the invention.

Reference in the specification to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment, nor are such embodiments exclusive of each other.

Conventional CT (Computerized Tomography) systems typically are a ring-shaped system (for example a set of detectors arrayed in a ring configuration) through which a patient is passed. Nuclear Medicine (NM) systems commonly are floor-mounted systems that rotate detectors around a patient.

Figure 1:
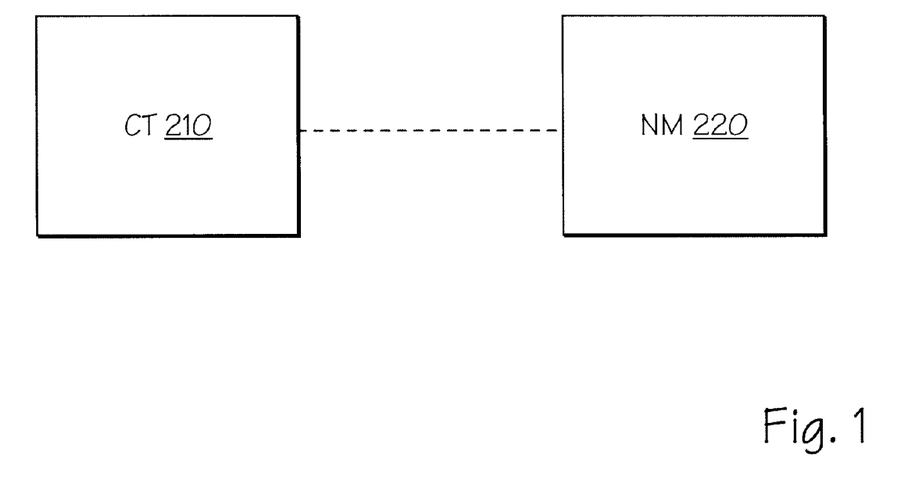
FIG. 1 illustrates a combination of a CT system 210 and an NM system 220 in block diagram form.

FIG. 1 illustrates a combination of a CT system 210 and an NM system 220 in block diagram form. Represented in the figure is a link between the two systems allowing a patient to be moved from one system to the other without disturbing the physical position of the patient. Preferably, a patient may be arranged on a bed, table, or platform, which may in turn be used during measurements by both systems.

Figure 2:
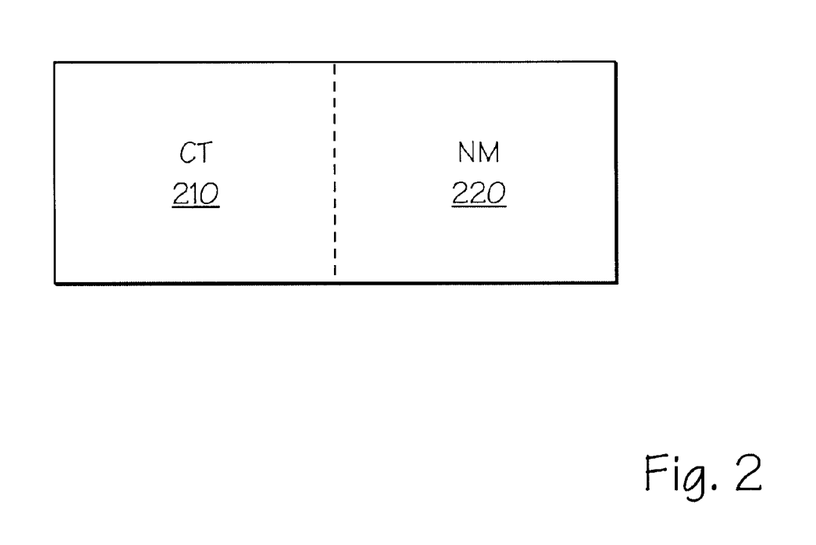
FIG. 2 illustrates an alternate embodiment of a combination of a CT system 210 and an NM system 220 in block diagram form.

FIG. 2 illustrates an alternative embodiment of a combination of a CT system 210 and an NM system 220 in block diagram form. In this embodiment, the two systems are more closely coupled physically, such that very little space separates the CT system 210 from the NM system 220, and they may be thought of as one integrated system.

Figure 3:
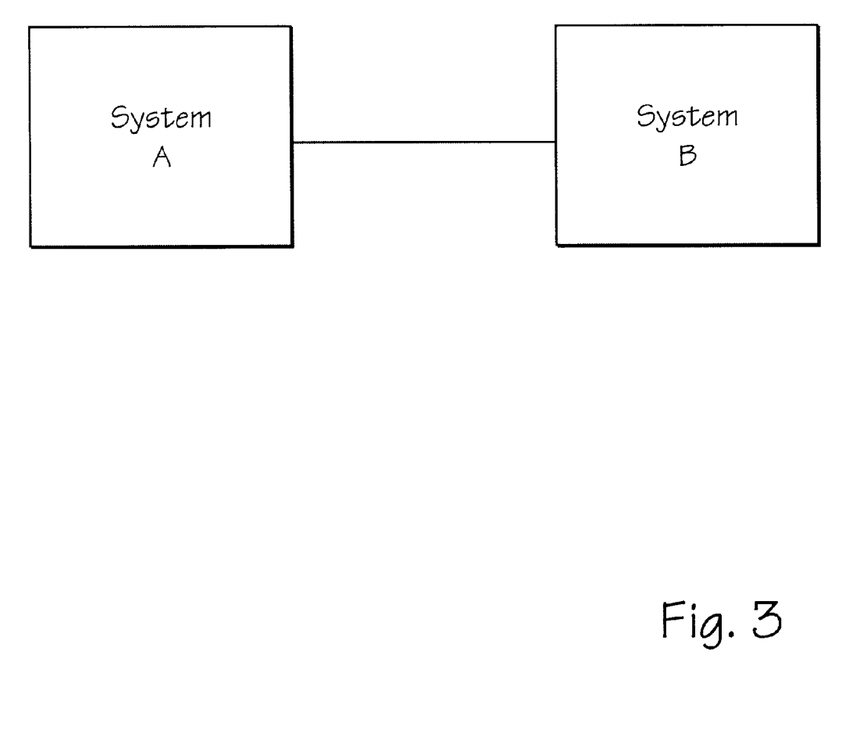
FIG. 3 illustrates a broader conception of the block diagram of FIG. 2, in which a System A and a System B are linked.

FIG. 3 illustrates a broader conception of the block diagram of FIG. 2, in which a System A and a System B are linked. System A may be a CT system, NM system, general x-ray system, sonogram system, ultrasound system, MRI system, or any other type of system for acquiring images of a live patient. Likewise, system B may be a NM system, a MRI system, general x-ray system, sonogram system, ultrasound system, a CT system, or any other type of system for acquiring images of a live patient. Preferably, system A will utilize a first modality, such as x-ray scanning and system B will utilize a second modality, such as nuclear medicine scanning.

Figure 4A:
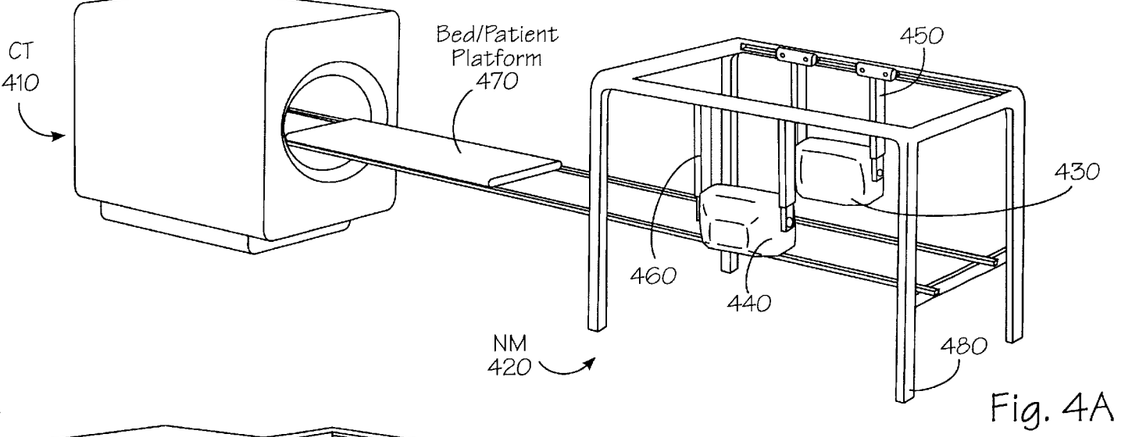
FIG. 4A illustrates one embodiment of a combined CT system and NM system.

FIG. 4A illustrates one embodiment of a CT system combined with an NM system in a perspective view. CT 410 is a CT system. NM 420 is an NM system having an overhead gantry. NM 420 includes NM detection cameras 430 and 440. NM detection camera 430 is connected to NM frame 480 by support structure 450. Likewise, NM detection camera 440 is connected to NM frame 480 by support structure 460.

Bed 470 is, in one embodiment, a combination NM bed and CT bed. In alternate embodiments, bed 470 may be a bed originally designed for use with a CT system or a bed originally designed for use with an NM system. In one embodiment, Bed 470 is designed such that the NM bed may move independently of the CT bed. The NM bed is what the patient rests on when the systems are operated. When the patient is moved into the NM system, the NM bed moves the patient into the system, while the CT bed stays outside the NM system. When the patient is moved into the CT system, the CT bed moves into the CT system, and the NM bed mimics the movement of the CT bed, thereby moving the patient into the CT system. This process of moving the NM bed into the CT system may be accomplished by linking control of the CT bed to control of the NM bed when a patient is to be moved into the CT system, or by programming the controls of the NM bed to move in a predetermined fashion which mimics movement of the CT bed.

In one embodiment, bed 470 is controlled by a workstation such as a computer (not shown) coupled to both the CT system 410 and NM system 420. In an alternate embodiment, a CT bed is controlled by a workstation coupled to CT system 410 and a NM bed is controlled by a workstation coupled to NM system 420. In integrating the two systems (CT 410 and NM 420), the NM bed may be controlled by the workstation of the NM system 420 to mimic the movements of the CT bed when the patient is to be moved into the CT system 410. Similarly, the CT bed may be controlled by the workstation of the CT system 410 to mimic an NM bed for purposes of moving the patient into the NM system. When both beds are present, both the NM bed and the CT bed may be thought of as components of bed 470, when only one bed is present, that bed constitutes the bed 470.

In an alternative embodiment, Bed 470 may be a bed suitable for use in an NM system 420, and may also be used in a CT system 410 without the CT bed. In such an embodiment, there is no need for slaving the NM bed to a CT bed, though the NM bed may need to be controlled in a manner that causes it to mimic the behavior of a CT bed for which the CT system was originally designed. Likewise, a CT bed may be suitable for use in both a CT system 410 and an NM system 420 such that an NM bed need not be supplied. In some embodiments, a bed supplied with a CT system 410 may not be suitable for use with the NM system 420, or a bed supplied with a NM system 420 may not be suitable for use with the CT system 410, thus requiring that one bed be controlled to mimic the other bed as described above. To the extent that beds are controlled by workstations which also control the rest of the system, the beds may be said to be operatively coupled to the rest of the system. This will typically involve some form of physical or electronic coupling allowing for the control to occur, such as a cable for transmitting instructions from the workstation to the bed.

Figure 4B:
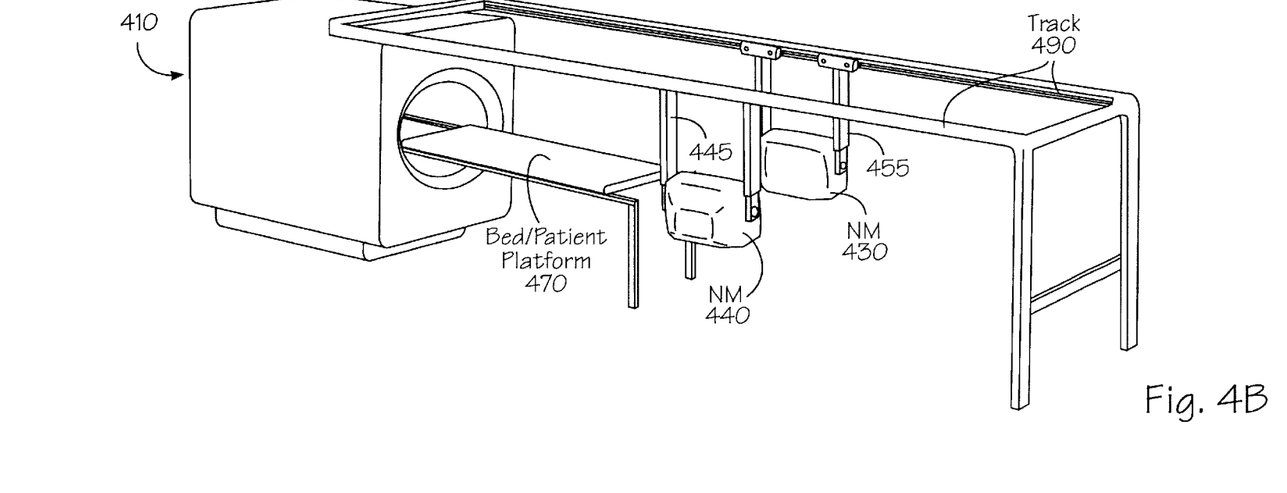
FIG. 4B illustrates an alternate embodiment of a combined CT system and NM system.

Turning to FIG. 4B, an alternative embodiment of a combination NM and CT system is illustrated. In this system, track 490 is an overhead gantry or track upon which support structures 455 and 445 may be moved, thereby moving detection cameras 440 and 430. As a result, the NM components may be moved to the location of the bed 470, thus requiring less range of motion for the bed 470. Furthermore, because the overhead gantry frees up much space traditionally required by an NM system, this configuration allows for the possibility of building the tracks into a space already available around an existing CT system. As a result, investments by medical facilities in existing CT systems need not be discarded in an attempt to create a dual mode imaging system.

Figure 5:
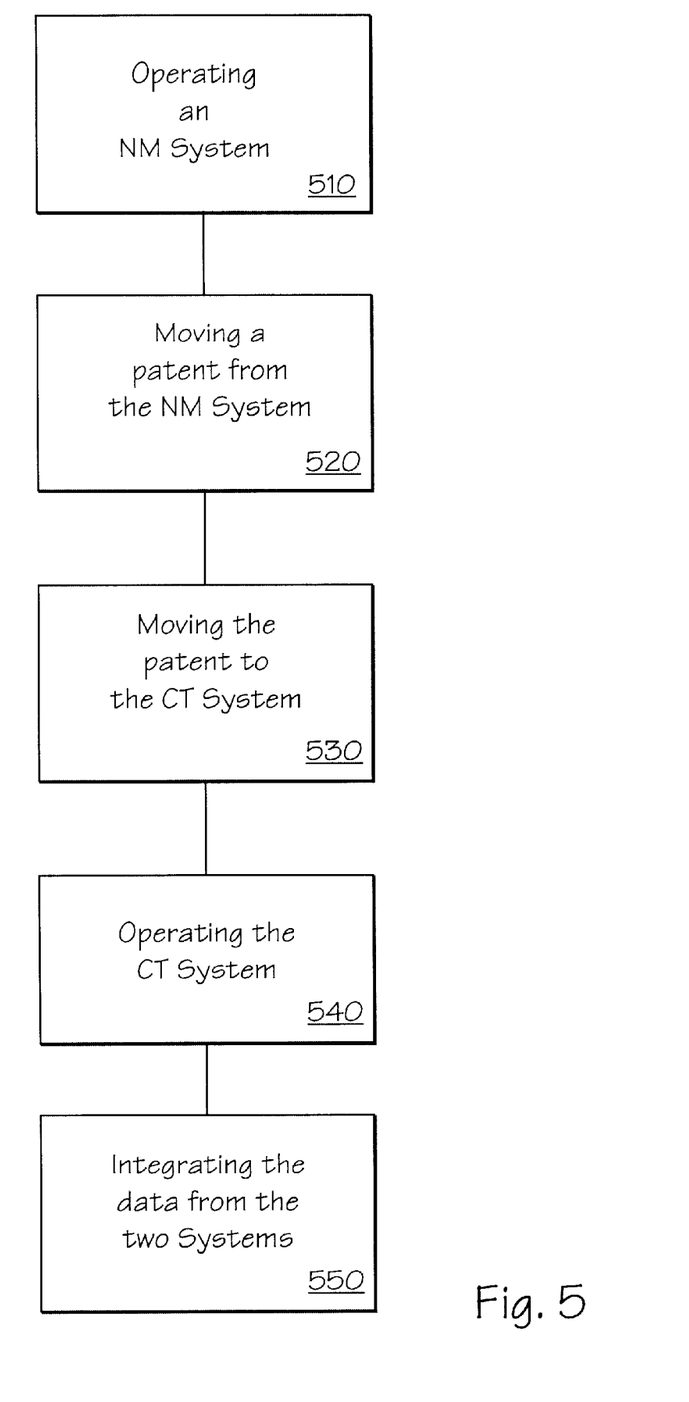
FIG. 5 illustrates a method of operating a dual mode system.

Turning to FIG. 5, an embodiment of a method of operating a dual mode imaging system is illustrated. At block 510, the NM system (such as NM 420) is operated, and one set of image data is collected. At block 520, the patient is moved out of the NM system. At block 530, the patient is moved into the CT system (such as CT 410). This may or may not involve slaving, coordinating, or synchronizing an NM bed to a CT bed as described earlier with regard to bed 470 in FIG. 4A. At block 540, the CT system is operated, thereby obtaining a second set of image data. Finally, at block 550, the two sets of image data are integrated. If the patient has been reasonably still, the correlations between the two sets of image data should be high, resulting in enhanced data which synergistically combines the two sets of image data.

Figure 6:
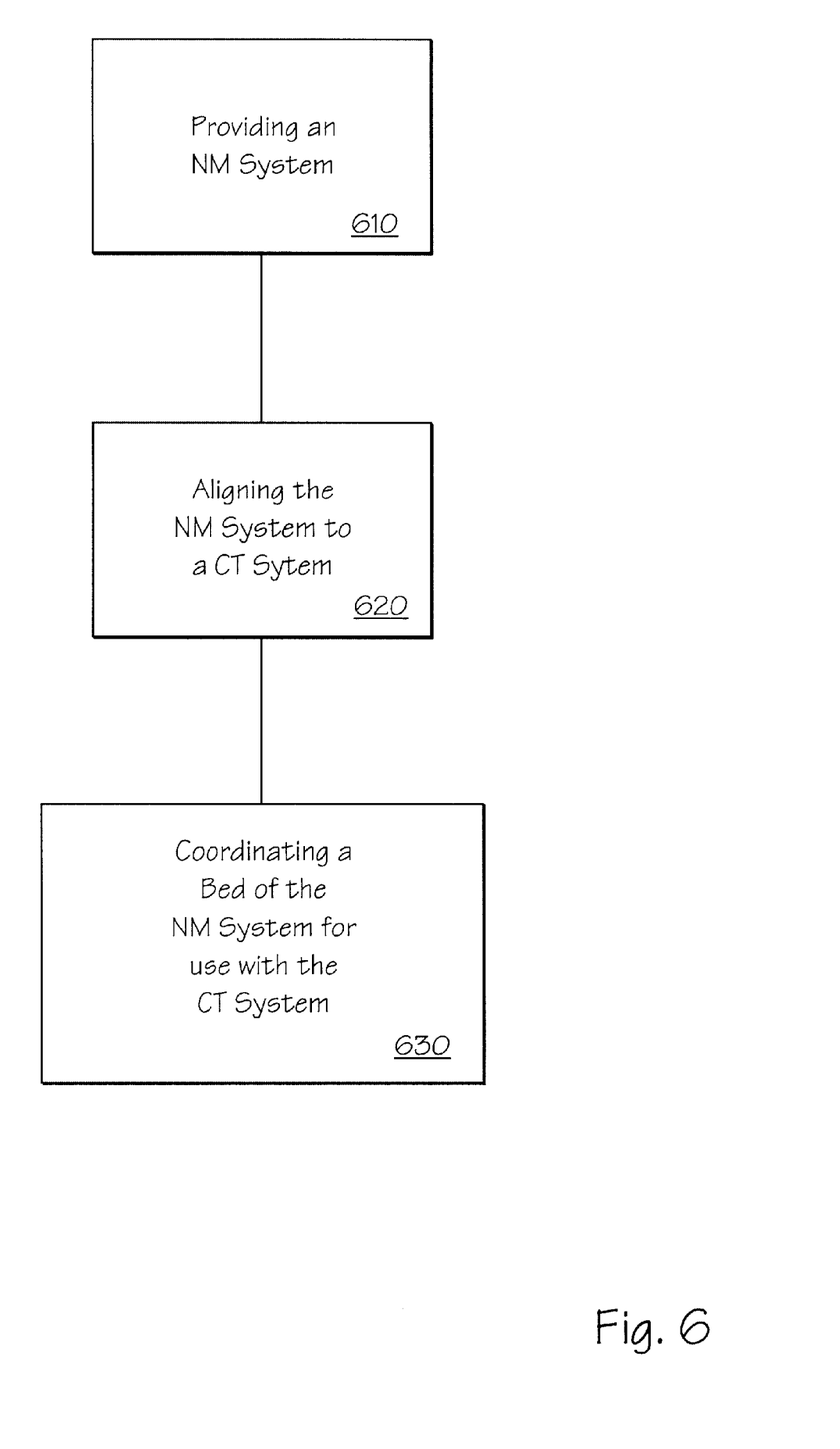
FIG. 6 illustrates a method of combining a NM system to a previously installed CT system to produce a dual mode system.

Turning to FIG. 6, one embodiment of a method of combining an NM system to a previously existing CT system, such as a CT system having a ring-shaped configuration for detectors, is illustrated. In block 610, a NM system is provided, such as an NM system using an overhead gantry configuration that may be combined with a CT system for example. At block 620, the NM system is aligned to the CT system, preferably allowing for a linear path through both the NM and CT systems. At block 630, the bed of the NM system is coordinated with the CT system, either by integrating control of the NM bed with the CT system, or by programming or configuring the NM bed to mimic the CT bed (such as moving both beds synchronously or in alignment).

As will be appreciated, the acts of the methods illustrated in FIGS. 5 and 6 need not be performed in the order depicted, and other acts may also be included. For example, in FIG. 5, the patient may be positioned on the NM bed and then moved into the NM system prior to operating the NM system. Likewise, the CT system may be operated first, and then the NM system operated. In either case, the CT bed may be used to support the patient instead. With regard to FIG. 6, both a NM system and a CT system may be provided and integrated together, rather than integrating an NM system to an already existing CT system. Likewise, a CT system may be integrated with an existing NM system.

Figure 7:
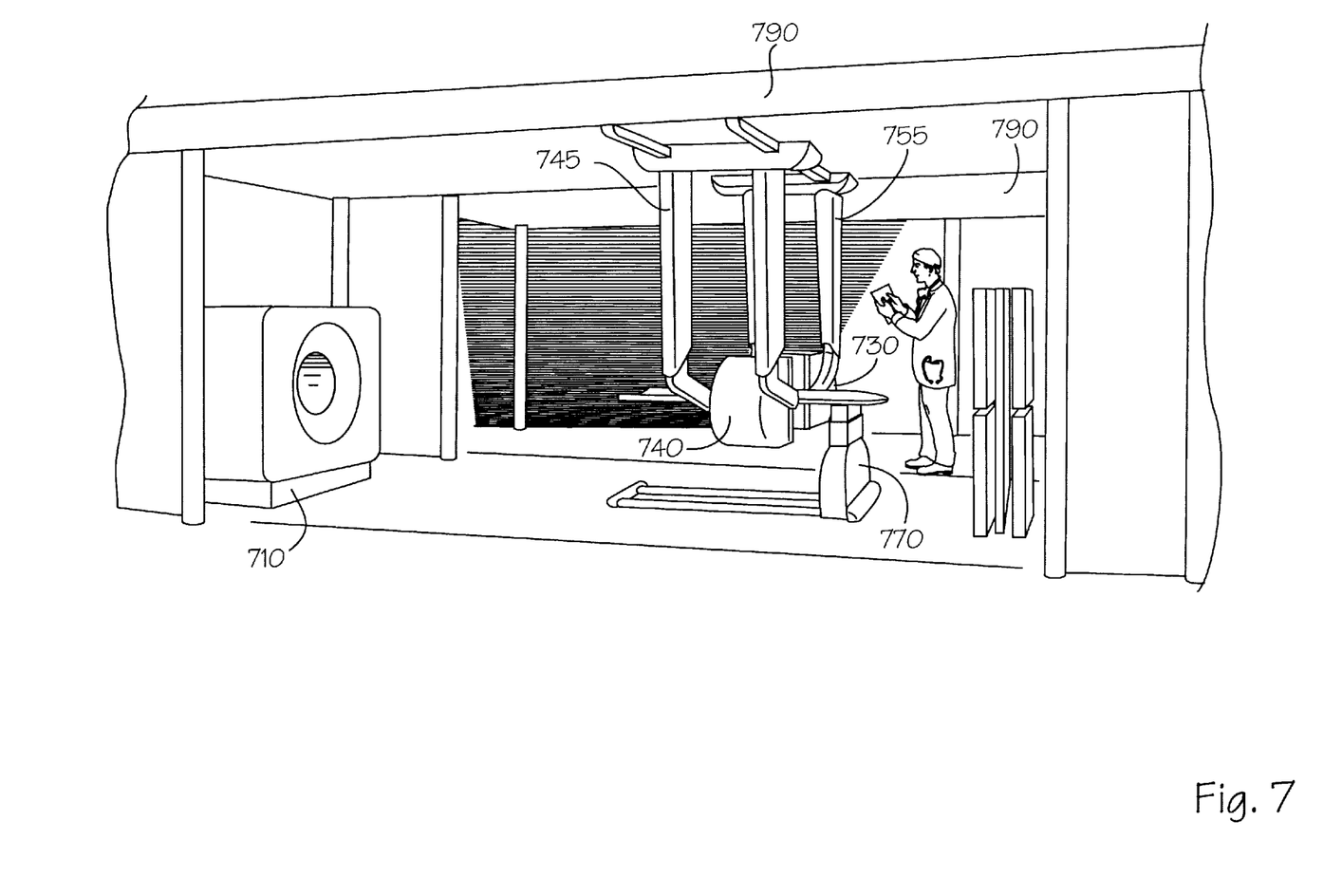
FIG. 7 illustrates a perspective view of a NM system combined with a CT system.

Turning to FIG. 7, a perpsective view of an alternate embodiment of a combination of a NM system and a CT system is illustrated. CT system 710 is a CT system with a ring-shaped configuration of detectors. Detection camera 730 (an NM detection camera) is suspended from one of tracks 790 by connection to support structure 755. Likewise, detection camera 740 (an NM detection camera) is suspended from the other of tracks 790 by support structure 745. Note that as illustrated, support structures 745 and 755 include common crossbars that link the two detection cameras 730 and 740 together through the support structures 745 and 755. Thus, detection cameras 730 and 740 may be moved around patient support table (bed) 770 when it is positioned between the two detection cameras. In one embodiment, support structures 745 and 755 are constructed such that they may be manipulated by extending or contracting and rotating various components to move detection cameras 730 and 740 to positions essentially describing a cylindrical or pipe shape around the patient and the portion of bed 770 in direct contact with the patient. As will be appreciated, support structures 745 and 755 may be moved along tracks 790 to various positions between the ends of tracks 790.

Bed 770 is, in one embodiment, a table supported on wheels, thus allowing it to be moved (or translated horizontally) into CT system 710, allowing CT system 710 to irradiate and scan the patient. As a result, this allows for movement of the patient from the NM system (between the detection cameras 730 and 740) to the CT system 710 and back in an undisturbed or relatively undisturbed manner. The patient need only be moved a short distance, and can be expected to remain relatively physically still or undisturbed, allowing for close correspondence between the locations of the patient's internal organs during both a CT scan and a NM scan. Following those scans, the image data collected from the two scans may be combined through use of software to provide integrated image data that often may provide a more detailed or richer view of the patient's internal organs.

Figure 8:
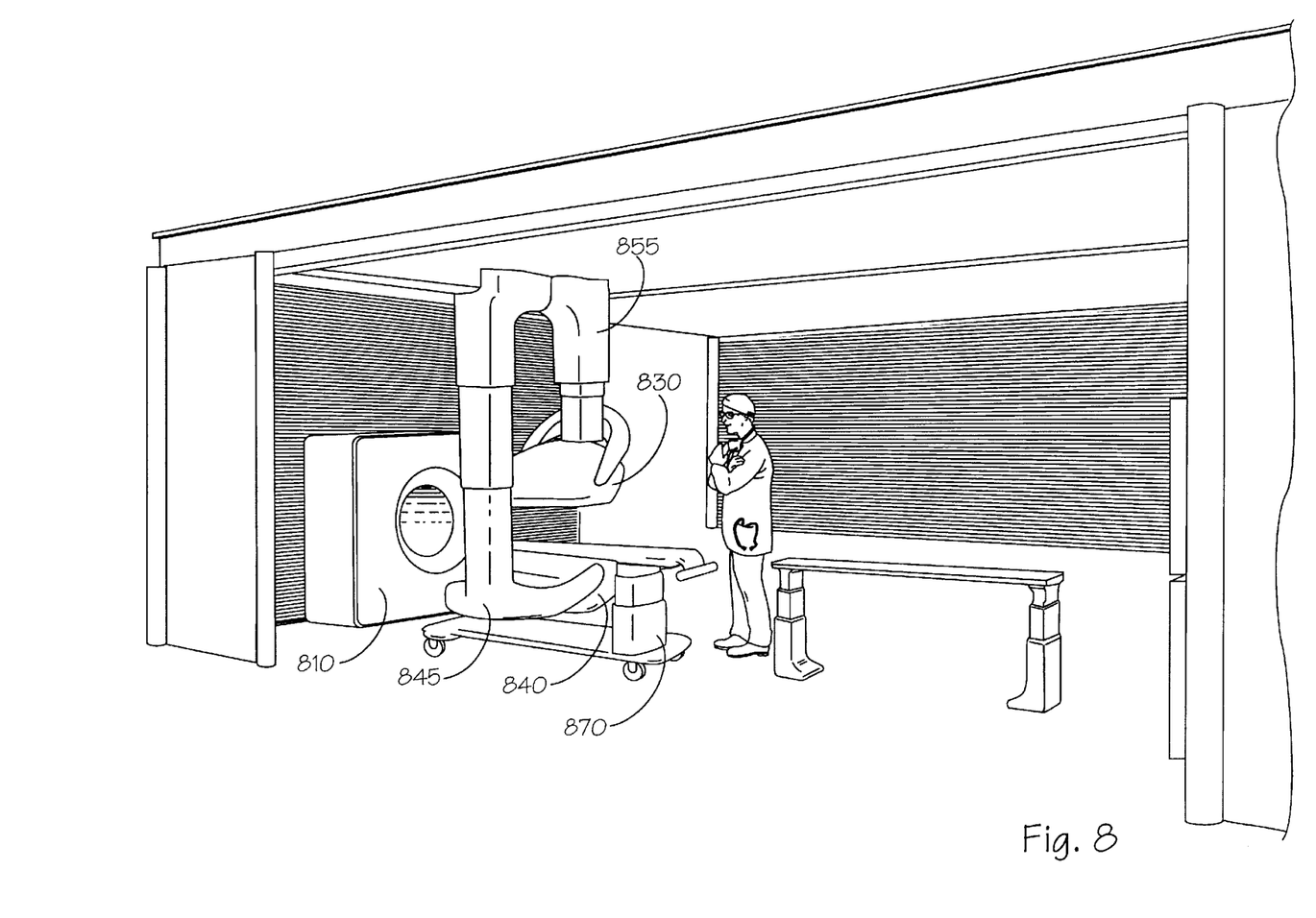
FIG. 8 illustrates a perspective view of an alternative combination of an NM system and a CT system.

Turning to FIG. 8, a perpsective view of another embodiment of a combination of a NM system and a CT system is illustrated. CT system 810 is a CT system utilizing a ring-shaped configuration of detectors. NM detection cameras 830 and 840 are suspended from the ceiling (or a suitable overhead support structure) through connection to support structures 845 and 855 respectively. Through manipulation of support structures 845 and 855, detection cameras 830 and 840 may be moved in a shape roughly describing a cylinder around bed (patient support table) 870 and a patient supported thereon. Likewise, bed 870 may be moved such that a patient may be moved into CT system 810 for purposes of performing a CT scan on the patient.

In both FIG. 7 and FIG. 8, human figures are included in the drawings for purposes of illustrating the scale or size of the apparatus or assembly in one embodiment. In the case of both detection cameras 730 and 740 (and support structures 745 and 755) and detection cameras 830 and 840 (and support structures 845 and 855) the motion of such components may be controlled by a workstation computer (not shown) and the motion of bed 770 or bed 870 may also be controlled by such a computer.

As will also be appreciated, substituting an MRI system or other type of conventional medical imaging system for either of the two systems (CT or NM) may be accomplished. Some combinations of systems, such as an MRI system and a NM system for example, may be more valuable to the medical community than other combinations, such as an MRI system and a CT system for example. Furthermore, three types of systems may be combined.

In the foregoing detailed description, the method and apparatus of the present invention has been described with reference to specific exemplary embodiments thereof. It will, however, be evident that various modifications and changes may be made thereto without departing from the broader spirit and scope of the present invention. The present specification and figures are accordingly to be regarded as illustrative rather than restrictive.

What is claimed is:

1. A method of creating a dual mode imaging system comprising:

aligning a NM system to a CT system, the NM system having a NM bed and an overhead gantry supporting a detector, the CT system having a CT bed; and coupling the NM bed to the CT bed when the CT system is used.

2. A method of forming a dual mode imaging system comprising:

providing a NM system, the NM system having an overhead gantry for supporting a detector;

providing a CT system;

providing a NM bed for the NM system;

providing a CT bed for the CT system;

linking control of the NM bed to control of the CT bed such that the NM bed moves in a manner corresponding to the movements of the CT bed when the CT system operates.

3. A method of operating a dual mode imaging system comprising:

operating a CT system with a patient on an NM bed within the CT system, the NM bed when in the CT system rests upon a CT bed and the NM bed moves synchronously with the CT bed when in the CT system;

moving the patient on the NM bed out of the CT system and into an NM system; and operating the NM system.

4. The method of claim 3 further comprising:

correlating data from the CT system to data from the NM system.

5. The method of claim 3 further comprising:

aligning an NM bed to a CT bed prior to operating the CT system;

moving the NM bed and the CT bed in alignment into the CT system prior to operating the CT system;

moving the NM bed and the CT bed in alignment out of the CT system after operating the CT system; and moving the NM bed out of alignment with the CT bed after moving the NM bed and the CT bed in alignment out of the CT system.

6. A system comprising:

a CT system having a ring configuration; and a NM system having an overhead gantry, the NM system aligned with the CT system such that a patient is transported from the NM system to the CT system in a physically undisturbed manner.

7. The system of claim 6 further comprising:

a NM bed for moving a patient into the NM system for scanning and for moving the patient into the CT system for scanning.

8. The system of claim 6 further comprising:

a CT bed for moving the patient into the CT system for scanning; and a NM bed for moving a patient into the NM system for scanning and for moving the patient into the CT system for scanning, the NM bed configured to mimic the motion of the CT bed.

9. A system comprising:

a patient bed for supporting a patient;

a first system for scanning a patient using a first modality, the first system including a ring configuration defining an examination region for receiving the patient bed along a first examination axis;

a second system for scanning a patient using a second modality, the second system having an overhead gantry system supporting a detector operatively proximate to an examination region for receiving the patient bed along a second examination axis generally aligned with the first examination axis; and means for moving a patient in an undisturbed manner on the patient bed between the first system and the second system along the generally aligned first examination axis and the second examination axis.

* * * * *